United States Patent [19]

Schneider et al.

[11] 4,224,245
[45] Sep. 23, 1980

[54] METHOD OF MAKING 1-(ALKOXYPHENYL)-5-(PHENYL)BIGUANIDE COMPOUNDS WHICH ARE USEFUL AS AGRICULTURAL FUNGICIDES

[75] Inventors: Louis Schneider, Elizabeth; Bruce M. Resnick, West Paterson, both of N.J.

[73] Assignee: GAF Corporation, New York, N.Y.

[21] Appl. No.: 33,244

[22] Filed: Apr. 25, 1979

[51] Int. Cl.³ .......................................... C07C 129/16
[52] U.S. Cl. .................................. 260/565; 260/564 B
[58] Field of Search ........................... 260/565, 564 B

[56] References Cited

U.S. PATENT DOCUMENTS

| | | | |
|---|---|---|---|
| 2,704,710 | 3/1955 | Sprung | 260/565 |
| 3,222,398 | 12/1965 | Brown et al. | 260/565 |
| 4,137,332 | 1/1979 | Brown et al. | 424/326 |

FOREIGN PATENT DOCUMENTS

| | | | |
|---|---|---|---|
| 716560 | 10/1954 | United Kingdom | 260/565 |
| 773410 | 4/1957 | United Kingdom | 260/565 |

OTHER PUBLICATIONS

Wheeler, Henry L. et al., J. Am. Chem. Soc., vol. 25, pp. 719-722 (1903).

Primary Examiner—Natalie Trousof
Assistant Examiner—L. Hendriksen
Attorney, Agent, or Firm—Walter C. Kehm; Walter Katz

[57] ABSTRACT

The present invention provides an improved method of making 1-(alkoxyphenyl)-5-(phenyl)biguanide compounds which are useful as agricultural fungicides, having the formula:

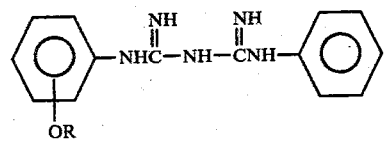

where R is alkyl, linear of branched, having from 1-14 carbon atoms; and acid addition salts thereof.

The method comprises the steps of (a) alkylating a nitrophenol with a suitable alkyl halide in a reaction solvent to form an alkoxynitrobenzene intermediate, (b) reducing the nitro group of the itermediate in situ by catalytic hydrogenation to form an alkoxyaniline, and (c) condensing the alkoxyaniline with phenyldicyandiamide to form the desired biguanide as the acid addition salt.

The invention also includes a novel isolation and purification procedure for obtaining purified biguanide acid addition salts and purified free biguanide base.

14 Claims, No Drawings

METHOD OF MAKING 1-(ALKOXYPHENYL)-5-(PHENYL)BIGUANIDE COMPOUNDS WHICH ARE USEFUL AS AGRICULTURAL FUNGICIDES

BACKGROUND OF THE DISCLOSURE

1. Field of the Invention

This invention relates to 1-(alkoxyphenyl)-5-(phenyl)biguanide compounds which are useful as agricultural fungicides, and, more particularly, to an improved method of making such compounds.

2. Description of the Prior Art

U.S. Pat. No. 4,137,332 discloses 1-(alkoxyphenyl)-5-(phenyl)biguanide compositions for use as agricultural fungicides. However, the method of synthesis given therein for such compounds is not suitable for commercial manufacture of these compounds.

SUMMARY OF THE INVENTION

The present invention provides an improved method of making fungicidal 1-(alkoxyphenyl)-5-(phenyl)biguanide compounds having the formula:

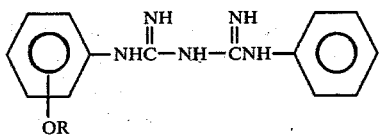

where R is alkyl, linear or branched, having from 1-14 carbon atoms; and acid addition salts thereof.

Preferably, R is a linear alkyl group having from 6-12 carbon atoms, in the para position, and most preferably, R is $C_8$. The best mode compound is 1-(p-n-octaoxyphenyl)-5-(phenyl)biguanide.

The method comprises the steps of (a) alkylating a nitrophenol with a suitable alkyl halide in a reaction solvent to form an alkoxynitrobenzene intermediate, (b) reducing the nitro group of the intermediate in situ by catalytic hydrogenation to form an alkoxyaniline, and (c) condensing the alkoxyaniline with phenyldicyandiamide to form the desired biguanide as the acid addition salt.

The invention also includes a novel isolation and purification procedure for obtaining purified biguanide acid addition salts and purified free biguanide base.

DETAILED DESCRIPTION OF THE INVENTION

The present method provides an improved, commercial process for preparing the desired fungicidal biguanide compounds as compared to the synthesis described in U.S. Pat. No. 4,137,332. The novel method of the invention offers considerable economic advantage over the previous method disclosed in said patent. In particular, the synthetic route made available herein is more readily adaptable to continuous manufacture of the desired biguanide compounds on an industrial scale and in a more economical manner.

The process of the invention is illustrated in the chemical flow chart which follows hereinafter.

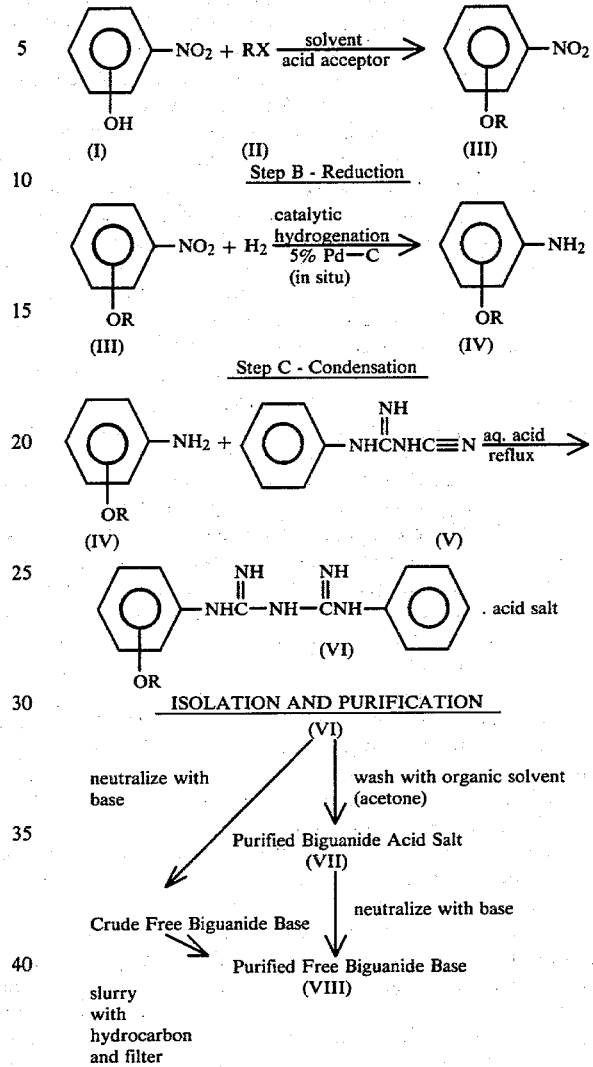

Step A in the process involves alkylation of a nitrophenol (I) with an alkyl halide (II) to provide an alkoxynitrobenzene (III). The alkyl halide has the formula RX, where R is a linear or branched alkyl group having from 1-14 carbon atoms, preferably from 6-12 carbon atoms, and, optimally, 8 carbon atoms. X is a halogen, e.g. chloro, bromo or iodo, and, preferably, chloro or bromo. The nitrophenol can have the nitro and hydroxy groups either ortho, meta or para to each other. The para position is preferred. Both starting reactants are commercially available or may be readily prepared by known methods.

The reaction is run in a suitable reaction solvent, preferably one in which at least one of the reactants is soluble, and optimally, in which both are soluble. Suitable reaction solvents include such known solvents as dimethylformamide, methylpyrrolidone, dimethylsulfoxide, toluene and the like. The preferred solvent is dimethylformamide. The reaction mixture includes an acid acceptor, such as a mild base, for example, potassium carbonate, which can absorb the acid-by-product of the alkylation. The reactants usually are present in about equal molar amounts, and the reaction is run at a somewhat elevated temperature, e.g. about 100°–150° C.

After completion of the reaction, the salts byproducts preferably are filtered and washed with additional solvent. The mother liquor then is used as the in situ reactant for the next step, and the solvent washes are recycled to the next batch as the reaction solvent.

Step B in the process involves reduction by hydrogenation of the nitro group of the alkoxynitrobenzene intermediate (III) in situ to the corresponding amino group to provide an alkoxyaniline (IV). By carrying out the reduction step in the same solvent as used in the alkylation step, it is not necessary to isolate intermediate (III) during Step A, except for removal of the salts by filtration. Furthermore, hydrogenation can be effected at rather high concentrations of (III) to solvent; for example, concentrations upwards of 45% have been used very successfully. Preferably, catalytic hydrogenation is employed, using, e.g. 5% palladium-on-carbon at about 75°–80° C. at a pressure of 75–80 psig.

Step C in the process involves condensation of the alkoxyaniline (IV) with phenyldicyandiamide (V) to provide the desired 1-(alkoxyphenyl)-5-(phenyl)biguanide. Phenyldicyanidiamide reactant is prepared by reacting sodium dicyanamide with diazotized aniline under alkaline conditions in water, and acidifying the triazene intermediate, as described in J. Am. Chem. Soc. 25, 719 (1903).

The condensation preferably is carried out in aqueous acid in alcohol solvent at reflux temperatures for several hours. Generally hydrochloric acid is used, although other inorganic and organic acids, such as hydrobromic acid, hydroiodic acid, sulfuric acid, nitric acid, phosphoric acid, acetic acid, methyl sulfuric acid, benzene sulfonic acid, and p-toluene sulfonic acid may be used as well. The product of the condensation is the acid addition salt of the biguanide compound.

Synthesis of the biguanide compounds by the sequence of Steps A, B and C affords the fungicidal product in high yield, generally at least 70% overall. The product may be used as such to prepare fungicidal compositions by formulation with an inert carrier. However, it is preferable to isolate and purify the biguanide compounds for commercial use.

Two alternative routes may be used for this purpose, as shown on the flow chart. In the first technique the crude biguanide acid addition salt (VI) is washed with a suitable purification solvent, preferably acetone, methyl ethyl acetone and the like, to remove organic impurities, leaving the purified biguanide acid addition salt (VII) as the product, which may be formulated directly into fungicidal compositions. The purified acid salt also may be converted to the purified free biguanide base (VIII) by neutralization with aqueous base which also may be used as the active ingredient in a fungicidal composition.

Alternatively, (VI) may be neutralized directly with aqueous base to provide the crude free biguanide base (IX) which can be purified by slurrying with a suitable solvent to solubilize the organic impurities without dissolving the biguanide. Hydrocarbons, either straight chain or branched, or mixtures thereof, having about 5–10 carbon atoms, are preferred for this purpose. Hexane is considered an optimum purification solvent in this procedure. The slurry is filtered and the purified free biguanide base (VIII) is isolated after further washing with hexane and drying in a vacuum oven.

EXAMPLE 1

Synthesis of 1-(p-n-Octaoxyphenyl)-5-(Phenyl)Biguanide Hydrochloride (a) p-Octaoxynitrobenzene Into a 2 l. flask was charged a mixture of p-nitrophenol (278 g., 2.0 mole), chlorooctane (310.8 g., 2.09 mole), potassium carbonate (145.2 g., 1.05 mole) in dimethylformamide (DMF) (556 g.) as a solvent. The reaction mixture then was heated at 130°–135° C. for 4 hrs. The progress of the reaction was monitored by gas-liquid chromatography (glc) analysis. The residue salts then were filtered and washed twice with 400 cc. of DMF. The mother liquor, which weighed 967 g., contained 442 g. of the desired intermediate. The combined washes, which weighed 963 g., contained an additional 52.1 g. of product. The total yield of intermediate was 494.3 g. of 98% purity, or 484.4 g. of the compound (96.5% yield). The DMF washes were recycled to the next batch as the reaction solvent.

(b) p-Octaoxyaniline

Into a 1 l. pressure reactor was charged the reaction product from step (a) above, namely, 600 cc of a 46% solution of p-octaoxynitrobenzene in DMF (587 g., 1.01 mole) and 3.8 g. of 5% palladium-on-carbon catalyst. The reactor then was purged three times with nitrogen at room temperature at a pressure of 60 psig and then twice with hydrogrn at the same pressure. The reactor temperature then was raised to 80° C. and hydrogen was admitted to maintain a constant pressure of 75–80 psig for 5 hrs. with intermittent heating and cooling. Finally, the reaction mixture was cooled to 250° C., vented, purged with nitrogen, and the catalyst separated by filtration.

The DMF solvent then was stripped under vacuum at 50-75 mm at a pot temperature of 67°–105° C. A total of 327 g. (95%) of the solvent was recovered for recycling to step (a) as the wash solvent. The yield of crude product was 243 g. (95.4% purity by glc analysis). (c) Into a 2 l. flask was charged p-octaoxyaniline (243 g., 91% purity, 1.0 mole) and 980 cc of ethanol. Thereafter, during a ½ hour period at 25°–30° C., a total of 109.7 g. of concentrated hydrochloric acid was added followed by phenyldicyandiamide (176.0 g., 1.1 mole). The reaction mixture then was heated at a reflux temperature of 75° C. for 6 hours. The reaction product was cooled to ice-bath temperature and filtered to give 390 g. of a solid product (93.5% yield) m.p. 114°–118° C.

EXAMPLE 2

Isolation of Purified 1-(p-n-Octaoxyphenyl)-5-(Phenyl)Biguanide Hydrochloride

The product of Example 1 (390 g.) was washed twice with 200 cc of acetone to provide 375 g. of the purified biguanide hydrochloride (m.p. 210°–212° C.), identified by NMR [broad band $\beta$ 9–10 (1H); multiplet 6.6-7.8 (14H); triplet $\delta$ 3.8 (J=5 Hz, 2H); multiplet $\delta$ 0.8–2.0 (15H)].

EXAMPLE 3

Isolation of Purified 1-(p-n-Octaoxyphenyl)-5-(Phenyl)Biguanide

The purified biguanide hydrochloride of Example 2 (375 g) was neutralized with 2550 cc of 2% aqueous sodium hydroxide at 45°-50° C. The free, purified biguanide was agitated for 1 hr. at 45°-50° C., cooled to 25°-30° C., filtered and water washed until neutral. The wet cake was dried to give 340 g. of purified product m.p. 120°-121° C.

EXAMPLE 4

Isolation of Purified Free Biguanide Base (Alternative Procedure)

The reaction product of Example 1 was neutralized by drowning it into 2550 cc of 2% aqueous sodium hydroxide maintained at 45°-50° C. The crude, neutralized biguanide then was agitated for 1 hr. at 45°-50° C., cooled to 25°-30° C., filtered and water washed until the pH of the filtrate was 7.5-8.0. The crude wet cake weighed 784 g., which contained about 352.8g. of product on a dry basis (92.6% crude yield).

The crude product then was slurried with 1200 cc of hexane at 25°-30° C. for ¼ hr., filtered, and washed with an additional 600 cc of hexane. The thuspurified free biguanide base was dried in a vacuum oven at 50° C. The purified free biguanide base weighed 298 g. (78.2% yield from the p-octaoxyaniline). The melting point was 120°-121° C.

What is claimed is:

1. In a method for making 1-(alkoxyphenyl)-5-(phenyl)biguanide compounds having the formula:

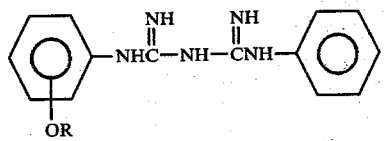

where R is alkyl, linear or branched, having from 1-14 carbon atoms, as the acid addition salts thereof, which comprises the steps of:
   (a) alkylating a nitrophenol with RX, where R is as defined above, and X is a halide, in a reaction solvent in the pressure of an acid acceptor, to form an alkoxynitrobenzene intermediate,
   (b) reducing said intermediate by catalytic hydrogenation to form the corresponding alkoxyaniline, and,
   (c) condensing the alkoxyaniline with phenyldicyandiamide in acid solution to form the desired biguanide as the acid addition salt, the improvement which comprises: carrying out steps (a) and (b) in situ in the same solvent selected from the group consisting of dimethylformamide, methylpyrrolidone, dimethylsulfoxide and toluene.

2. A method according to claim 1 which further includes the steps of isolating and purifying said acid addition salt.

3. A method according to claim 1 which further includes the steps of isolating and purifying the free biguanide base.

4. A method according to claim 1 wherein said purified acid addition salt is made by washing the crude product with a purification solvent.

5. A method according to claim 4 wherein said purification solvent is acetone or methyl ethyl ketone.

6. A method according to claim 4 wherein said purified acid addition salt is neutralized with a base to provide the purified free biguanide.

7. A method according to claim 1 wherein said reaction solvent is removed after Step (b).

8. A method according to claim 1 wherein R is alkyl having from 6-12 carbon atoms in the para position.

9. A method according to claim 1 wherein said biguanide is 1-(p-n-octaoxyphenyl)-5-(phenyl)biguanide.

10. A method according to claim 1 wherein said reaction solvent is dimethylformamide.

11. The method of isolating purified 1-(alkoxyphenyl)-5-(phenyl)biguanide acid addition salts as defined in claim 1 which comprises washing the crude products thereof with a purification solvent to remove organic impurities thereof.

12. The method according to claim 11 wherein said purification solvent is acetone or methyl ethyl ketone.

13. The method according to claim 11 further including the step of neutralizing the purified acid addition salt to provide the purified free biguanide.

14. Purified hydrochloride acid addition salt of 1-(p-n-octaoxyphenyl)-5-(phenyl)biguanide as defined in claim 1 having a melting point of at least 210°-212° C., and an NMR spectra which is [broad band δ 9-10 (1H); multiplet 6.6-7.8 (14H); triplet δ 3.8 (J=5 Hz, 2H); multiplet δ 0.8-2.0 (15H)].

* * * * *